(12) United States Patent
Kuwahara et al.

(10) Patent No.: US 6,346,119 B1
(45) Date of Patent: Feb. 12, 2002

(54) GRAFT EQUIPPED WITH STENT

(75) Inventors: Kunio Kuwahara; Hideki Furuya; Hiroyuki Ikeda, all of Ichihara (JP)

(73) Assignee: Ube Industries, LTD, Yamaguchi (JP)

(*) Notice: Subject to any disclaimer, the term of this patent is extended or adjusted under 35 U.S.C. 154(b) by 0 days.

(21) Appl. No.: 09/463,220

(22) PCT Filed: Jul. 17, 1998

(86) PCT No.: PCT/JP98/03213

§ 371 Date: Feb. 17, 2000

§ 102(e) Date: Feb. 17, 2000

(87) PCT Pub. No.: WO99/04727

PCT Pub. Date: Feb. 4, 1999

(30) Foreign Application Priority Data

Jul. 25, 1997 (JP) .................... 9-199534

(51) Int. Cl.[7] .................... A61F 2/06
(52) U.S. Cl. .................... 623/1.13
(58) Field of Search .................... 606/198; 623/1, 623/1.22, 22.26, 1.49, 1.32, 1.52, 1.11, 1.12–1.16

(56) References Cited

U.S. PATENT DOCUMENTS

| | | | | |
|---|---|---|---|---|
| 4,776,337 A | * | 10/1988 | Palmaz | 623/1 |
| 4,892,539 A | * | 1/1990 | Koch | 623/1 |
| 5,123,917 A | * | 6/1992 | Lee | 623/1 |
| 5,211,658 A | * | 5/1993 | Clouse | 623/1 |
| 5,282,823 A | * | 2/1994 | Schwartz et al. | 606/198 |
| 5,824,037 A | * | 10/1998 | Fogarty et al. | 623/1 |
| 6,174,328 B1 | * | 1/2001 | Cragg | 623/1.15 |

FOREIGN PATENT DOCUMENTS

| | | |
|---|---|---|
| JP | 1-274756 | 11/1989 |
| JP | 7-24072 | 1/1995 |
| JP | 9-173468 | 7/1997 |
| JP | 9-285550 | 11/1997 |

* cited by examiner

Primary Examiner—Henry J. Recla
Assistant Examiner—(Jackie) Tan-Uyen T. Ho
(74) Attorney, Agent, or Firm—Armstrong, Westerman, Hattori, McLeland, & Naughton, LLP

(57) ABSTRACT

A graft with a stent, includes: a stent composed of a resilient wire having a supporting frame comprising a wire having a zigzag shape forming top and bottom portions; and tubes being made of plain woven of polyester resin fibers and having a thickness of 20 $\mu$m to 100 $\mu$m. The tubes are disposed between inner surface and outer surface of the stent, and the inner tube surface and the outer tube surface are partially adhered to each other by a polyester resin. The graft is free from hindrance of blood from flowing by kink and/or arctation in a corner such as an arched portion, a curved portion, and meandering portion, is resistant to expansion and contraction and bending, and is fit to a shape of a blood vessel of a human body. The graft is usable for a total percutaneous intravascular surgery because it can be inserted into a sheath having a small diameter because of a thin artificial blood vessel, and is prone not to have leakage from a connection with a blood vessel. The stent does not directly contact an organism and is capable of being indwelt in an organism.

8 Claims, 3 Drawing Sheets

GRAFT EQUIPPED WITH STENT

TECHNICAL FIELD

The present invention relates to a graft with a stent such as an artificial blood vessel with a stent, and to a graft with a thin stent which is free from transudabon of blood at the connection with a blood vessel and hindrance of blood from flowing by kink and/or arctation.

BACKGROUND ART

At present, a tubular film with a stent is mainly used for an endovascular surgery of aneurysm or the like. When a blood vessel is narrow, celiotomy is required to insert a sheath in a blood vessel from a thick portion thereof. Thus, a total percutaneous intravascular surgery is sometimes difficult.

Since a tubular film with a stent on the inner surface of the tubular film is most popular, various kinds of materials forming the stent, such as metals, plastics or the like, directly contact organism and/or blood, which sometimes causes a problem.

In the aforementioned tubular film with a stent, the stent is sometimes fixed on the inner or outer surface of the tubular film by the use of an anastomotic thread and a needle. In this case, the tubular film is occasionally holed partially by the needle, which causes transudation of blood.

As an example in which a stent is fixed on a tubular film or in which a in which a coating layer comprising a tetrafluoroethylene resin porous film is disposed on the inner and outer surfaces of a tubular structure composed of an elastic wire rod.

JP-A-8-141090 discloses an indwelling type stent, which comprises a stent body being formed so as to have an almost tubular shape, having a plurality of openings passing from the outer surface to the inner surface of the tubular shape, and being shrinkable in the diametral direction; a thermoplastic resin layer covering the stent, and a tubular cover covering the outer and/or inner periphery of the stent body, closing up the openings, and fixed to the thermoplastic resin layer. Since, the stent body is covered by a thermoplastic resin layer; the stent does not directly contact an organism. However, it is may be possible that the stent cannot move flexibly in accordance with a movement of organism when it is indwelt, for example, a movement such as expansion and contraction in a longitudinal or diametral direction because the stent is completely fixed to the tubular cover.

JP-A-9-173468 discloses a covered stent being provided with, inside a stent support, a coating layer being substantially free from the pores which allow cells to pass therethrough and, outside thereof, a coating layer in which fibers are entangled each other irregularly, and a method for producing the same.

The present invention is intended to provide a graft with a thin stent and a method for producing the same. The stent does not directly contact an organism and is capable of being indwelt in an organism. The graft is free from hindrance of blood from flowing by kink and/or arctation in a corner such as an arched portion, a curved portion, and meandering portion; is resistant to expansion and contraction and bending; is fit for a shape of a blood vessel of a human body; and is usable for a total percutaneous intravascular surgery.

DISCLOSURE OF INVENTION

According to the present invention, there is provided a graft with a stent, comprising:

a stent composed of a resilient wire forming a zigzag shaped supporting frame made of a wire; said zigzag shaped supporting frame having top and bottom portions; and tubes each being made of plain woven of polyester resin fibers and each having a thickness of 20 μm to 100 μm;

the tubes being disposed respectively on the inner surface and the outer surface of the stent, and the inner surface of the outer tube and the outer surface of the inner tube being partially adhered to each other by a polyester resin.

It is preferable that the. inner surface of the outer tube and the outer surface of the inner tube are adhered to each other by injecting a polyester resin from the side of the outer surface of the outer tube.

Specifically, the zigzag shape of the stent terminates in end portions. The stent is disposed between the inner tube and the outer tube, the stent, inner tube, and outer tube being concentrically arranged. The outer surface of the inner tube and the inner surface of the outer tube are adhered to each other by a polyester resin only at spaced discrete points within the boundaries of the stent.

It is more preferable that the inner surface of the outer tube and the outer surface of the inner tube are partially adhered to each other at the top and/or the bottom portions of the stent

BEST MODE FOR CARRYING OUT THE INVENTION

Figure 1:
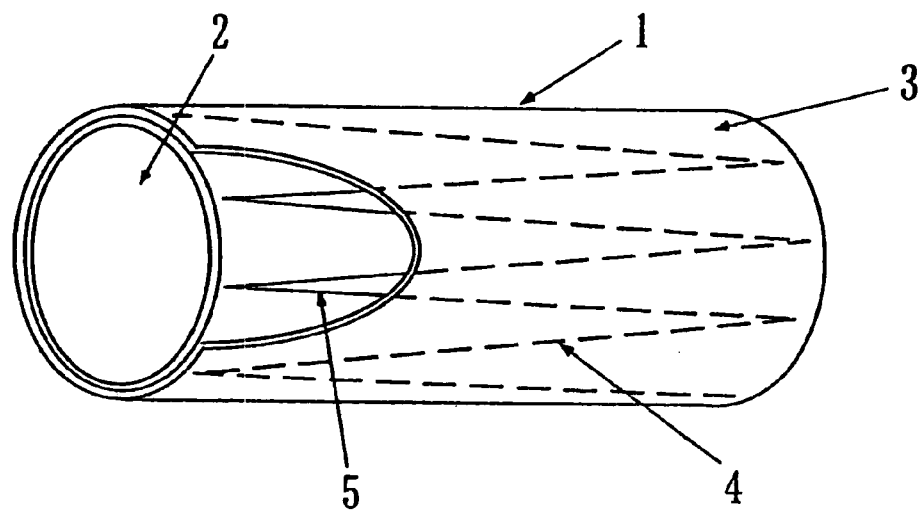
FIG. 1 is a perspective view showing an example of an artificial blood vessel with a stent in which the inner surface of the outer tube and the outer surface of the inner tube are not adhered to each other and a shape in which a part of the outer tube surface is removed.

A graft with a stent of the present invention is hereinbelow described, by using as an illustrative example an artificial blood vessel with a stent.

The present invention is directed to a graft with a stent, said stent composed of a resilient wire forming a zigzag shaped supporting frame made of a wire; said zigzag shaped supporting frame having top and bottom portions, being provided with tubes on both the inner surface and the outer surface of said stent. The tubes are made of plain woven of polyester resin fibers and have a thickness of 20 μm–100 μm, preferably 20 μm–70 μm, more preferably 20 μm –60 μm, furthermore preferably 30 μm–50 μm. The inner surface of the outer tube and the outer surface of the inner tube are partially adhered to each other by a polyester resin.

When a thickness of the tube is smaller than 20 μm, there sometimes occurs thread slippage even if the inner surface of the outer tube and the outer surface of the inner tube are partially adhered to each other by a polyester resin.

When a thickness of a tube is larger than 100 μm, it is difficult to insert the tubes into a sheath having a small diameter, which sometimes makes a total percutaneous surgery impossible.

Further, it is preferable that the inner surfaces of the outer tube and the outer surface of the inner tube are preferably adhered to each other by injecting a polyester resin from the side of the outer surface of the outer tube. This does not wound the inner tube surface during injecting an adhesive. Therefore, blood is not transuded to a gap between the inner surface of the outer tube and the outer surface of the inner tube. Since the inner surface of the outer tube and the outer surface of the inner tube are partially adhered to each other at top and/or bottom portions of the stent, the stent is fixed between the inner tube and the outer tube without affecting adversely on an initial shape of the stent. This preferably prevents a stent from having displacement in a longitudinal or diametral direction or being offset in one direction.

The aforementioned tubes preferably have the outside diameter of 5–45 mm, more preferably 7–40 mm, and furthermore preferably 8–40 mm. When the outside diameter is larger than 45 mm, it is sometimes difficult to insert the tubes into a thin sheath.

An artificial blood vessel with a stent of the present invention is preferably able to insert into a 24 Fr sheath and preferably used for an intravascular surgery, particularly total percutaneous intravascular surgery.

As the aforementioned stent, there can be preferably used a tubular structure composed of a resilient wire forming a zigzag shaped supporting frame made of a wire; said zigzag shaped supporting frame forming top and bottom portions, and having the following characteristics.

Supporting Frame
- (A1) Thickness=0.10–0.50 mm, more preferably 0.15–0.50 mm
- (A2) Length (blood flow direction)=0.5–3.0 cm, more preferably 0.7–3.0 cm, furthermore preferably 0.7–2.5 cm wherein the above-mentioned term "length" represents the shortest distance between a line linking a top portion with the next top portions and a line linking a bottom portion and the next bottom portions, and the thickness represents a diameter of a wire at the thickest portion.

As the aforementioned supporting frame, there can be used a continuous spiral structure of a continuous wire which has a zigzag shape forming top portions and bottom portions and preferably has 1–150 windings, more preferably 1–100 windings, and furthermore preferably 2–100 windings; and/or preferably 1–150 rings, more preferably 1–100 rings, and furthermore preferably 2–100 rings, each of which are made of a wire having a zigzag shape forming top portions and bottom portions. The continuous spiral structure and the rings are preferably used in combination with each other.

In the aforementioned supporting flames, top portions and adjoined bottom portions thereof may be combined with each other by a cross-linking and/or a clamping material. Combining top portions of the supporting frame with adjacent bottom portions thereof in the supporting frame improves a shape-maintaining ability against contraction.

In the aforementioned stent, a wire used at the ends of the supporting frame preferably has a thickness different from that of the wire in a portion between the two ends. Particularly, when a wire at the ends of the supporting frame is thicker than that in a portion between the ends, it is easy to insert an artificial blood vessel with a stent into a sheath and to fix the stent inside the blood vessel because the end portion has a strong resilience, the stent may have a moderate resilient-recovering force, and the stent may be adapted to a blood vessel smoothly because of the resistance against bending. Thus, such a structure has excellent properties.

As a material for the aforementioned resilient wire, there is preferably used a stainless steel, a shape memory alloy such as an alloy of titanium-nickel compound, a metal such as a tantalum-titanium compound, a shape memory resin, or the like.

The aforementioned resilient wire may be subjected to a coating treatment by the use of a thermoplastic fluororesin, a thermoplastic copolymer such as polyolefin (e.g. low density polyethylene, low density polypropylene, low density ethylene-α-olefin copolymer), polyester (e.g., low melting point polyester), polycarbonate, polyurethane, or an antithrombotic material such as heparin, collagen, acetylsalicylic acid, and gelatin.

As a clamping material, there can be used polyethylene, polypropylene, polyolefin such as ethylene-α-olefin copolymer, polyamide, polyurethane, poly(ethylene terephthalate), poly-(butylene terephthalate), poly(cyclohexane terephthalate), polyester polyethylene-2,6-naphthalate, fluororesin such as PTFE and ETFE, thermoplastic resin fiber such as a shape memory resin, stainless steel, a shape memory alloy such as a titanium-nickel compound alloy, or a metallic wire such as a tantalum-titanium compound. The thermoplastic resin fiber, the shape memory alloy, or the metallic wire may be subjected to a coating treatment by the use of a thermoplastic fluororesin, a thermoplastic copolymer such as polyolefin (e.g., low density polyethylene, low density polypropylene, low density ethylene-α-olefin copolymer), polyester (e.g., low melting point polyester), polycarbonate, polyurethane, or an antithrombotic material such as heparin, collagen, acetylsalicylic acid, and gelatin.

As the aforementioned polyester resin fiber, there is preferably used a fiber of a polyester resin such as poly(ethylene terephthalate), poly(butylene terephthalate), poly(cyclohexane terephthalate), and polyester polyethylene-2,6-naphthalate. Particularly, poly(ethylene terephthalate) is preferable because it is chemically stable, has a high durability, has less histionic reactions, and is excellent in mechanical properties such as tensile strength.

The aforementioned polyester resin preferably has a glass transition temperature of 50° C. or more, particularly 60° C. or more. In the case of polyester resin whose glass transition temperature is lower than 50° C., such a polyester resin is not preferably since it may be lowered by a bodily temperature occasionally.

The polyester resin fiber is preferably made by twisting monofilaments of preferably 0.01–5 denir, more preferably 0.03–3 denir, and furthermore preferably 0.5–1 denir. The number of monofilaments is preferably in the range from several number to some hundred, more preferably 10–700, furthermore preferably 10–100.

The polyester resin fiber may be subjected to a coating treatment by the use of an antithrombotic material such as heparin, collagen, acetylsalicylic acid, and gelatin.

It is preferable to use tubes made of plain fabric of regularly woven polyester resin fibers, and have pores through which cells can substantially pass. It is preferable that the tubes are not subjected to a crimp processing.

The present invention is hereinbelow described in details with reference to the drawings and the Examples. However, the present invention is by no means limited to those examples and figures.

FIG. 1 is a perspective view showing an example of an artificial blood vessel with a stent in which the inner surface of the outer tube is not partially connected with the outer surface of the inner tube. The outer tube 3 was partially cut out. In an artificial blood vessel 1 with a stent, the tubes 2 and 3 are provided in the inner side and the outer side of the stent 4, respectively.

Figure 2:
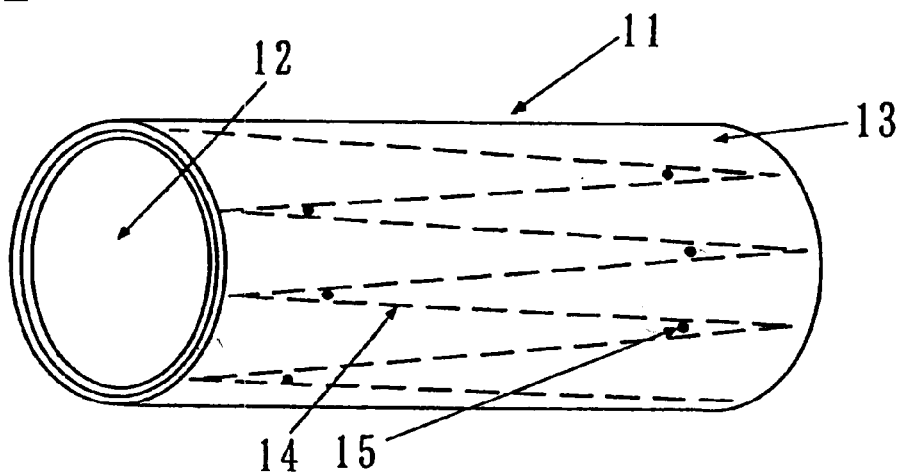
FIG. 2 is a perspective view showing another artificial blood vessel with a stent according to the present invention.

FIG. 2 is a perspective view showing an example of an artificial blood vessel with a stent of the present invention. In an artificial blood vessel 11 with a stent, the tubes 12 and 13 are provided in the inner side and the outer side of the stent 14, respectively. The adhered portion 15 is a one in which the intermediate portion between the outer surface of the tube 12 and the inner surface of the tube 13 at top and bottom portions of the stent 14 is adhered by a polyester resin being injected from the outer surface of the tube 13.

Figure 3:
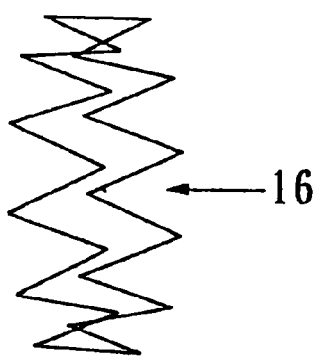
FIG. 3 is a perspective view showing an example of a ring-shaped wire to be used for an artificial blood vessel with a stent of the present invention.

FIG. 3 is a partial perspective view of a ring-shaped wire in a form of zigzag having top portions and bottom portions.

Figure 4:
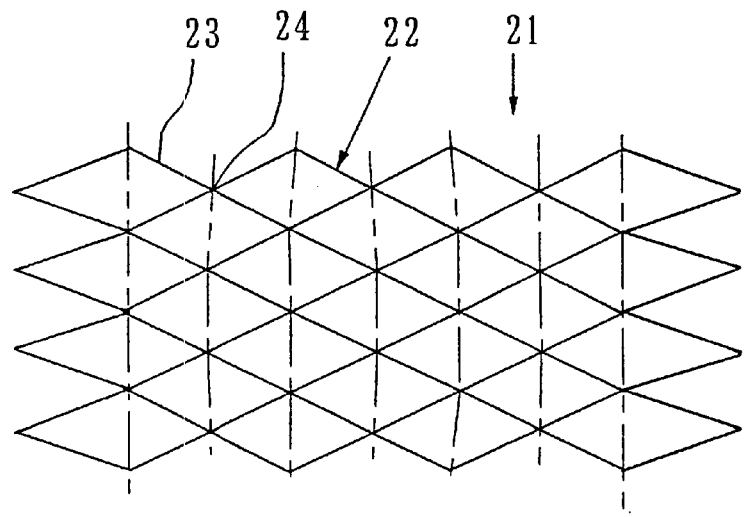
FIG. 4 is a partial development of an example of a stent to be used for an artificial blood vessel with a stent of the present invention.

FIG. 4 shows a partial development of the stent 21. The stent 21 is provided with a supporting frame 22 and a clamping material 24. The supporting frame 22 is composed of a ring-shaped wire 23 of a zigzag shape forming top portions and bottom portions. In the supporting frame 22, top portions of the supporting frame 22 are connected with adjacent bottom portions thereof in the supporting frame 22 by means of the clamping material 24.

Figure 5:
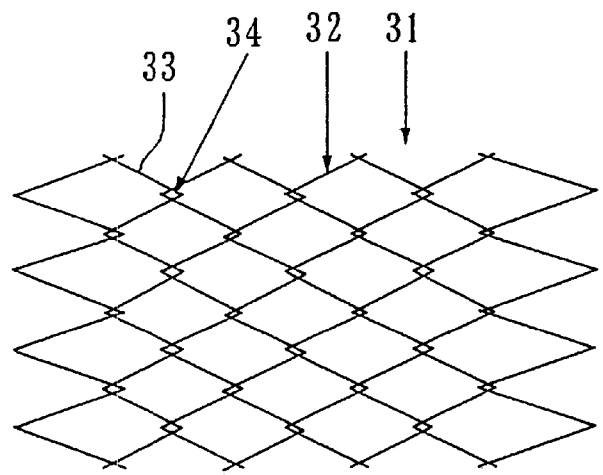
FIG. 5 is a partial development of another stent to be used for an artificial blood vessel with a stent of the present invention.

FIG. 5 shows a partial development of a stent 31. The stent 31 is provided with a supporting frame 32. The supporting frame 32 is composed of a ring-shaped wire 33 of a zigzag shape forming top portions and bottom portions. Top portions of the supporting frame 32 are connected with adjacent bottom portions thereof in the supporting frame 32. The connected portion is shown as an intersection 34.

Figure 6:
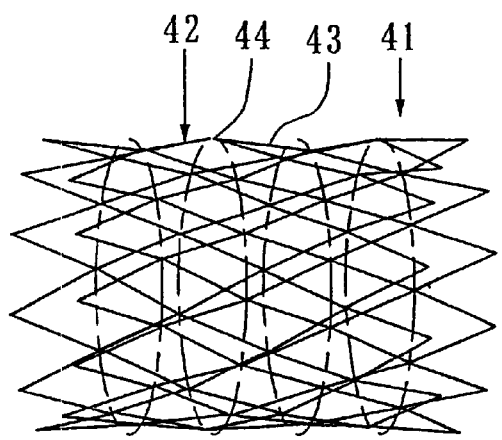
FIG. 6 is a perspective view of another stent to be used for an artificial blood vessel with a stent of the present invention.

FIG. 6 shows a partial perspective view of a stent 41. The stent 41

FIG. 6 shows a partial perspective view of a stent 41. The stent 41 is provided with a supporting frame 42 and a clamping material 44. The supporting frame 42 is composed of a ring-shaped wire 43 of a zigzag shape forming top portions and bottom portions. The top portions of the supporting frame 42 are connected with adjacent bottom portions of the supporting frame 42 by means of a clamping member 44.

Figure 7:
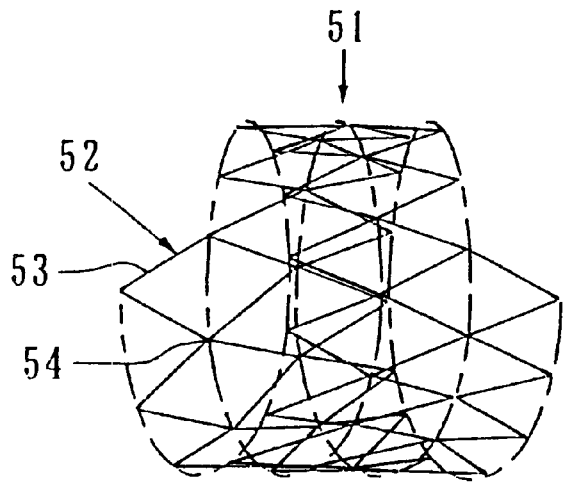
FIG. 7 is a perspective view of another stent to be used for an artificial blood vessel with a stent of the present invention.

FIG. 7 shows a partial perspective view of a stent 51. The stent 51 is provided with a supporting frame 52 and a clamping material 54. The supporting frame 52 is composed of a wire 53 which has a continuous spiral structure of a plurality of windings and a zigzag shape forming top portions and bottom portions.

Figure 8:
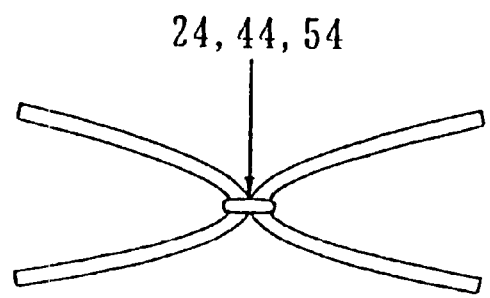
FIG. 8 is a side view of an example of a clamping material of FIGS. 4, 6, and 7. 6,and7.

FIG. 8 shows a partial side view of clamping materials 24, 44, and 54. The clamping materials 24, 44, and 54 each connects a top portion of the supporting frame and an adjacent bottom portion of the supporting frame. The top portions and the bottom portions of the support abut against each other.

Figure 9:
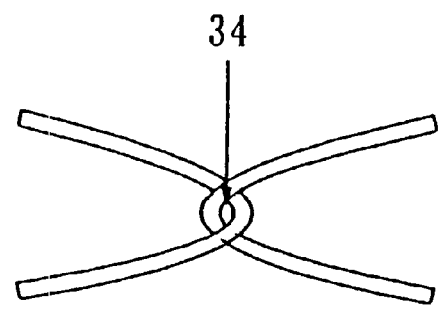
FIG. 9 is a side view of an example of an intersection of a supporting frame of FIG. 5.

FIG. 9 shows an intersection 34 where the top portion of a supporting member is connected with the adjacent bottom portion thereof in the supporting member by crossing. The top portion of the supporting member is connected with the bottom portion of the supporting member at the intersection 34.

A tube made of plain woven of thermoplastic resin fibers was measured for a thickness by a digimatic micrometer in each of Examples and Comparative Examples shown below.

EXAMPLE 1

As a thermoplastic resin fiber, there was used a thread obtained by twisting 0.7 denir monofilaments of poly (ethylene terephthalate). A tube having the outside diameter of 20 mm was made of a plain weave made by the use of 253 thermoplastic resin fibers of 50 denir for threads extending in a longitudinal direction and thermoplastic resin fibers of 40 denir for threads extending in a peripheral direction. The tube had a thickness of 50 $\mu$m.

A stent having a supporting frame composed of a ring-shaped wire having a diameter of 0.4 mm and of zigzag portion forming the top and bottom portions was inserted into an outer tube. Then, the end portions of the outer tube were folded inside so as to hold the stent to obtain an artificial blood vessel A with a stent having a form shown in FIG. 1.

A stainless stick having a diameter of 20 mm was inserted into the artificial blood vessel A with a stent and subjected to a thermal treatment at 160° C. for 10 minutes. Then, a molten polyester resin was injected into an intermediate portion of the inner tube and the outer tube at the top and bottom portions of the zigzag shape of the ring-shaped wire so as to connect the inner tube and the outer tube by adhesion. Thus, an artificial blood vessel B with a stent having a form shown in FIG. 2 was obtained.

It was possible to insert the obtained artificial blood vessels A and B each having a stent in a 24 Fr sheath.

A possible leakage of water in the artificial blood vessel B with a stent was observed. Water having a temperature of 37° C. was poured on the inner surface of the artificial blood vessel B with a stent under a pressure of 120 mmHg so as to observe leakage of water from the outer tube. There was observed no leakage of water from portions where the polyester resin was injected and where the tubes are adhered to each other.

In the artificial blood vessel B with a stent, no displacement of the stent was found in the artificial blood vessel B even when it was swished or expanded and contracted.

COMPARATIVE EXAMPLE 1

A stainless steel having a diameter of 20 mm was inserted into the artificial blood vessel A with a stent obtained in Example 1 and subjected to a thermal treatment at 160° C. for 10 minutes. Then, the inner surface of the artificial blood vessel was fixed to the outer surface at top and bottom portions of the stent forming a vessel C with a stent.

Leakage of water form the artificial blood vessel C was observed in the same manner as in Example 1. Water having a temperature of 37° C. was poured on the inner surface of the artificial blood vessel C under a pressure of 120 mmHg so as to observe leakage of water from the outer tube. There was found leakage of water spouting from a fixed portion, by sewing with a polyester thread (6–0), of the outer tube.

COMPARATIVE EXAMPLE 2

As a thermoplastic resin composition, twisted monofilaments of poly(ethylene terephthalate) of 0.7 denir. A plain weave made by the use of 1053 thermoplastic resin fibers of 50 denir for threads extending in a longitudinal direction and thermoplastic resin fibers of 100 denir for threads extending in a peripheral direction. The tube had a thickness of 180 $\mu$m.

A stent having a supporting frame composed of a ring-shaped wire having a diameter of 0.4 mm and having top and bottom portions was inserted into an outer tube. Then, the outer tube was folded inside so as to hold the stent to obtain an artificial blood vessel D with a stent having a form shown in FIG. 1.

A stainless stick having a diameter of 20 mm was inserted into the artificial blood vessel D with a stent and subjected to a thermal treatment at 160° C. for 10 minutes. Then, a molten polyester resin was injected into an intermediate portion of the inner tube and the outer tube at the top and bottom portions of the zigzag shape of the ring-shaped wire so as to connect the inner tube and the outer tube by adhesion. Thus, an artificial blood vessel E with a stent having a form shown in FIG. 2 was obtained.

It was difficult to insert the obtained artificial blood vessels D and E each having a stent in a 24 Fr sheath.

Industrial Applicability

A graft with a thin stent of the present invention is free from hindrance of blood from flowing by kink and/or arctation in a comer such as an arched portion, a curved portion, and meandering portion; is resistant to expansion and contraction and bending; is fit to a shape of a blood vessel of a human body; is usable for a total percutaneous intravascular surgery because R is a thin artificial blood vessel and can be inserted into a sheath having a small diameter; and is prone not to have leakage from a connection with a blood vessel. The stent does not directly contact an organism and is capable of being indwelt in an organism.

What is claimed is:

1. A graft with a stent, comprising:

a stent composed of an elastic wire rod having a supporting frame comprising a wire having a zigzag shape terminating in end portions; and an inner tube and an outer tube each made of plain woven polyester resin fibers and having a thickness of $20\mu$ to $100\ \mu m$, said stent being disposed between said inner tube and said outer tube;

said stent, inner tube, and outer tube being concentrically arranged, and an outer surface of the inner tube and an inner surface of the outer tube being adhered to each other by a polyester resin only at spaced discrete points within the boundaries of said stent.

2. A graft with a stent according to claim 1, wherein the outer surface of the inner tube and the inner surface of the outer tube are adhered to each other by injecting a polyester resin from an outer surface of the outer tube.

3. A graft with a stent according to claim 1 or 2, wherein the outer surface of the inner tube and the inner surface of the outer tube are only adhered to each other at top and/or bottom portions of the stent.

4. A graft with stent according to claim 1 or 2, wherein the graft is an artificial blood vessel.

5. A graft with stent according to claim 3, wherein the graft is an artificial blood vessel.

6. A graft with a stent according to any one of claims 1 or 2, wherein the wire having a zigzag shape comprises any or both of (i) a plurality of rings each comprising wire having a zigzag shape having top and bottom portions and (ii) a spiral comprising wire having a zigzag shape having top and bottom portions, adjacent top and bottom portions of the rings, spiral, or both, being connected to each other.

7. A graft with a stent according to claim 6, wherein said top and bottom portions of said zigzag shape of said wire of said rings, said spiral, or both said rings and said spirals, are connected to each other by clamping.

8. A graft with a stent according to claim 6, wherein said top and bottom portions of said zigzag shape of said wire of said rings, said spiral, or both said rings and said spirals, are connected to each other by crossing.

* * * * *